US00PP28918P3

(12) United States Plant Patent
Geibel

(10) Patent No.: US PP28,918 P3
(45) Date of Patent: Jan. 30, 2018

(54) ***PELARGONIUM* PLANT NAMED 'PACPEROSY'**

(50) Latin Name: *Pelargonium peltatum*
Varietal Denomination: Pacperosy

(71) Applicant: Martin Geibel, Dresden (DE)

(72) Inventor: Martin Geibel, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 44 days.

(21) Appl. No.: 14/999,457

(22) Filed: May 9, 2016

(65) Prior Publication Data

US 2017/0325387 P1 Nov. 9, 2017

(51) Int. Cl.
*A01H 5/02* (2006.01)

(52) U.S. Cl.
USPC ..... Plt./332

(58) Field of Classification Search
USPC ..... Plt./332
See application file for complete search history.

*Primary Examiner* — Susan McCormick Ewoldt
(74) *Attorney, Agent, or Firm* — C. A. Whealy

(57) ABSTRACT

A new and distinct Ivy Geranium plant named 'Pacperosy', characterized by its uniformly mounding, rounded and slightly cascading plant habit; moderately vigorous growth habit; freely basal branching habit; dark green-colored leaves; freely flowering habit; and large soft pink semi-double flowers that are positioned above and beyond the foliar plane.

1 Drawing Sheet

Botanical designation: *Pelargonium peltatum.*
Cultivar denomination: 'PACPEROSY'.

BACKGROUND OF THE INVENTION

The present invention relates to a new and distinct cultivar of Ivy Geranium plant, botanically known as *Pelargonium peltatum*, and hereinafter referred to by the cultivar name 'Pacperosy'.

The new Ivy Geranium plant is a product of a planned breeding program conducted by the Inventor in Dresden, Germany. The objective of the breeding program is to develop new vigorous Ivy Geranium plants with uniform plant habit and numerous attractive semi-double flowers.

The new Ivy Geranium plant originated from an open-pollination during the summer of 2009 of *Pelargonium peltatum* 'Pachane', disclosed in U.S. Plant Pat. No. 21,847, as the female, or seed, parent and an unknown selection of *Pelargonium peltatum* as the male, or pollen, parent. The new Ivy Geranium plant was discovered and selected by the Inventor as a flowering plant from within the progeny of the stated open-pollination in a controlled greenhouse environment in Dresden, Germany in June, 2010.

Asexual reproduction of the new Ivy Geranium plant by vegetative terminal cuttings in a controlled greenhouse environment in Dresden, Germany since December, 2010 has shown that the unique features of this new Ivy Geranium plant are stable and reproduced true to type in successive generations.

SUMMARY OF THE INVENTION

Plants of the new Ivy Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pacperosy'. These characteristics in combination distinguish 'Pacperosy' as a new and distinct Ivy Geranium plant:

1. Uniformly mounding, rounded and slightly cascading plant habit.
2. Moderately vigorous growth habit.
3. Freely basal branching habit.
4. Dark green-colored leaves.
5. Freely flowering habit.
6. Large soft pink semi-double flowers that are positioned above and beyond the foliar plane.

Plants of the new Ivy Geranium differ primarily from plants of the female parent selection in flower type and color as plants of the female parent selection have single-type flowers that are light purple in color.

Plants of the new Ivy Geranium can be compared to plants of the *Pelargonium peltatum* 'Paclill', disclosed in U.S. Plant Pat. No. 17,956. In side-by-side comparisons, plants of the new Ivy Geranium differ from plants of 'Paclill' in the following characteristics:

1. Plants of the new Ivy Geranium are more cascading than plants of 'Paclill'.
2. Plants of the new Ivy Geranium are not as vigorous as plants of 'Paclill'.
3. Plants of the new Ivy Geranium have more flowers per umbel than plants of 'Paclill'.
4. Plants of the new Ivy Geranium and 'Paclill' differ in flower color as plants of 'Paclill' have soft lavender-colored flowers.

BRIEF DESCRIPTION OF THE PHOTOGRAPH

The accompanying colored photograph illustrates the overall appearance of the new Ivy Geranium plant showing the colors as true as it is reasonably possible to obtain in colored reproductions of this type. Colors in the photograph may differ slightly from the color values cited in the detailed botanical description which accurately describe the colors of the new Ivy Geranium plant. The photograph comprises a side perspective view of a typical flowering plant of 'Pacperosy' grown in a container.

DETAILED BOTANICAL DESCRIPTION

The aforementioned photograph and following observations, measurements and values describe plants grown in 19-cm containers during the summer in a glass-covered greenhouse in Dresden, Germany and under cultural practices typical of commercial Ivy Geranium production. During the production of the plants, day temperatures ranged from 18° C. to 20° C., night temperatures averaged 18° C. and light levels ranged from 15 kilolux to 75 kilolux. Plants were pinched two times and were nine months old when the photograph and the detailed description were taken. In the detailed description, color references are made to The Royal Horticultural Society Colour Chart, 1995 Edition, except where general terms of ordinary dictionary significance are used.

Botanical classification: *Pelargonium peltatum* 'Pacperosy'.

Parentage:

*Female, or seed, parent.*—*Pelargonium peltatum* 'Pachane', disclosed in U.S. Plant Pat. No. 21,847.

*Male or pollen parent.*—Unknown selection of *Pelargonium peltatum*, not patented.

Propagation:

*Type.*—By vegetative terminal cuttings.

*Time to initiate roots, summer.*—About 18 days at temperatures about 20° C.

*Time to initiate roots, winter.*—About 22 days at temperatures about 20° C.

*Time to produce a rooted young plant, summer.*—About four weeks at temperatures about 20° C.

*Time to produce a rooted young plant, winter.*—About four weeks at temperatures about 18° C.

*Root description.*—Fine, fibrous; white in color.

*Rooting habit.*—Freely branching; dense.

Plant description:

*Plant and growth habit.*—Uniformly mounding, rounded and slightly cascading plant habit; densely foliated; moderately vigorous growth habit and moderate growth rate; freely basal branching habit with numerous lateral branches developing per plant.

*Plant height, to top of umbels.*—About 33 cm.

*Plant height, to top of foliar plane.*—About 25 cm.

*Plant width.*—About 60 cm.

*Lateral branches.*—Length: About 35 cm. Diameter: About 4 mm. Internode length: About 2 cm. Texture: Slightly pubescent. Color: Close to 147B.

Leaf description:

*Arrangement.*—Mostly opposite; simple.

*Length.*—About 3.5 cm.

*Width.*—About 5.5 cm.

*Shape.*—Palmately lobed.

*Apex.*—Pointed.

*Base.*—Cordate; imbricate.

*Margin.*—Entire, lobed.

*Venation pattern.*—Palmate.

*Texture, upper surface.*—Smooth, glabrous.

*Texture, lower surface.*—Sparsely pubescent along the veins.

*Color.*—Developing and fully expanded leaves, upper surface: Close to 137A; venation, close to 137A. Developing and fully expanded leaves, lower surface: Close to 146A; venation, close to 146B. Zonation pattern: Discernable on developing leaves. Intensity: Moderate. Location: About 2 cm from margin. Width: About 5 mm. Color: Close to 200A.

*Petioles.*—Length: About 3 cm. Diameter: About 1.5 mm. Texture, upper and lower surfaces: Glabrous, rough. Color, upper and lower surfaces: Close to 144A.

Flower description:

*Flower arrangement and flowering habit.*—Semi-double rotate flowers arranged in hemispherical umbels arising from apical leaf axils; umbels displayed above and beyond the foliar plane on strong peduncles; umbels and flowers face upright to outwardly; freely flowering habit; about six flowers per umbel and numerous umbels developing per plant.

*Fragrance.*—None detected.

*Flowering season.*—Early flowering habit, plants begin flowering about four months after planting; in the garden in Germany, flowering begins in May and continues until frost in the autumn.

*Flower longevity.*—Flowers last about six to ten days on the plant; umbels last about three to four weeks on the plant; flowers persistent.

*Umbel height.*—About 5 cm.

*Umbel diameter.*—About 9 cm.

*Flower diameter.*—About 5.5 cm.

*Flower depth (height).*—About 2 cm.

*Flower buds.*—Length: About 1 cm. Diameter: About 6 mm. Shape: Rounded. Color: Close to 146B.

*Petals.*—Quantity per flower: About 15 in several whorls; petals imbricate. Length: About 2.7 cm to 3 cm. Width: About 1.7 cm to 2 cm. Shape: Obovate. Apex: Rounded. Base: Cuneate. Margin: Entire. Texture, upper and lower surfaces: Smooth, glabrous; velvety; undulate. Color: When opening and fully opened, upper surface: Close to 75B; towards the base, close to 155D; venation, close to 74A; color becoming closer to 75C with development. When opening and fully opened, lower surface: Close to 75D; towards the base, close to 155D; venation, close to 75D.

*Petaloids.*—Quantity per flower: If present, up to three at the center of the flower. Length: About 1 cm to 1.5 cm. Width: About 5 mm to 15 mm. Shape: Irregular. Apex: Pointed to rounded. Base: Cuneate. Margin: Entire. Texture, upper and lower surfaces: Smooth, glabrous; velvety; crinkled. Color: When opening and fully opened, upper surface: Close to 75B; towards the base, close to 155D; venation, close to 74A; color becoming closer to 75C with development. When opening and fully opened, lower surface: Close to 75D; towards the base, close to 155D; venation, close to 75D.

*Sepals.*—Quantity per flower: About five arranged in a single whorl. Length: About 1 cm. Width: About 3 mm. Shape: Lanceolate. Apex: Acute. Margin: Entire. Texture, upper and lower surfaces: Slightly pubescent. Color, upper and lower surfaces: Close to 144A.

*Peduncles* (*umbel stems*).—Length: About 11 cm. Diameter: About 3 mm. Strength: Strong. Angle: Upright to outwardly slanted. Texture: Slightly pubescent. Color: Close to 146A.

*Pedicels* (*individual flower stems*).—Length: About 2.5 cm. Diameter: About 1 mm. Strength: Strong; flexible. Texture: Slightly pubescent. Color: Close to 146B.

*Reproductive organs*.—Androecium: Stamen quantity per flower: About eleven. Anther length: About 2 mm. Anther shape: Tubular. Anther color: Close to 59A. Pollen amount: Abundant. Pollen color: Close to 167A. Gynoecium: Pistil quantity per flower: One. Pistil length: About 1 cm. Stigma shape: Seven-parted. Stigma color: Close to 63B. Style length: About 3 mm. Style color: Close to 155D. Ovary color: Close to 138C. Seeds and fruits: Seed and fruit development have not been observed on plants of the new Ivy Geranium.

Disease & pest resistance: Plants of the new Ivy Geranium have not been observed to be resistant to pathogens and pests common to Ivy Geranium plants.

Temperature tolerance: Plants of the new Ivy Geranium have been observed to tolerate temperatures ranging from about 1° C. to about 35° C. to 40° C.

It is claimed:

1. A new and distinct Ivy Geranium plant named 'Pacperosy' as illustrated and described.

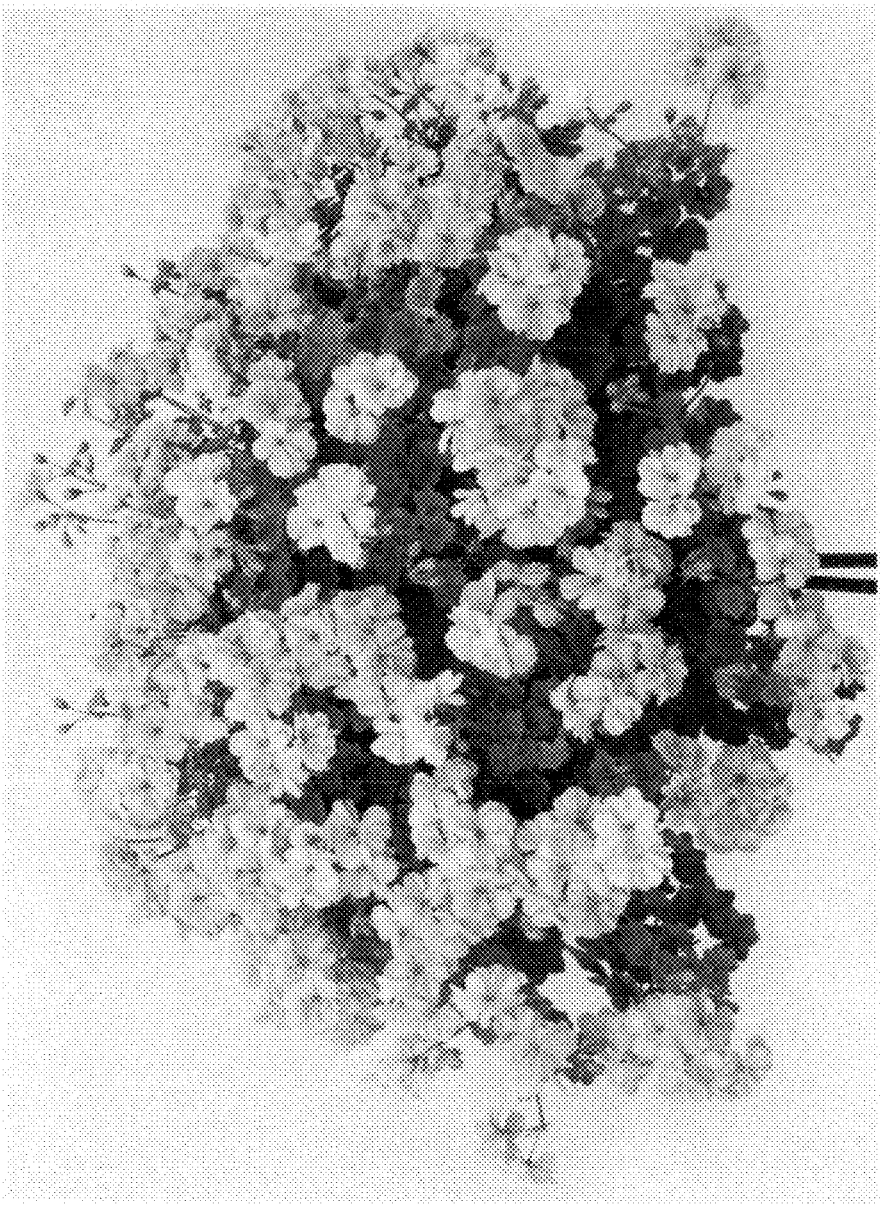

* * * * *